United States Patent [19]
Koike et al.

[11] Patent Number: 5,404,184
[45] Date of Patent: Apr. 4, 1995

[54] OPHTHALMIC LIGHT IRRADIATION APPARATUS

[75] Inventors: Chikashi Koike, Hino; Itaru Yoshizawa, Gamagori, both of Japan

[73] Assignee: Kowa Company Ltd., Japan

[21] Appl. No.: 994,987

[22] Filed: Dec. 22, 1992

[30] Foreign Application Priority Data

Dec. 26, 1991 [JP] Japan .................. 3-343775

[51] Int. Cl.$^6$ .............................................. A61B 3/00
[52] U.S. Cl. ...................................... 351/245; 351/205
[58] Field of Search ............... 351/245, 214, 205, 200, 351/246, 219; 359/875, 876

[56] References Cited

U.S. PATENT DOCUMENTS

| | | | |
|---|---|---|---|
| 4,976,528 | 12/1990 | Cuda | 359/875 |
| 5,000,562 | 3/1991 | Ichihashi et al. | 351/214 |
| 5,291,336 | 3/1994 | Miles | 359/875 |

Primary Examiner—William L. Sikes
Assistant Examiner—Hung Xuan Dang
Attorney, Agent, or Firm—Adams & Wilks

[57] ABSTRACT

An ophthalmic light irradiation apparatus includes a deflection member and an operating section for driving the deflection member to deflect a laser beam to the interior of a patient's eye. The operating member includes an operating lever, a fixed ball member affixed to the operating lever, and a movable ball member integrally mounted on one end of the operating lever and movably engaged with the fixed ball member. The movable ball member is offset along the axial direction of the operating lever, which is supported so that it can be tilted in a desired direction within a plane substantially orthogonal to the axis of the lever. Movement of the movable ball member produced by tilting the operating lever is divided into first and second orthogonal directions for transmission to the deflection member. The apparatus is structurally simple in construction and has good operability enabling the laser beam to be precisely controlled.

13 Claims, 4 Drawing Sheets

OPHTHALMIC LIGHT IRRADIATION APPARATUS

BACKGROUND OF THE INVENTION

1. Field of the Invention

This invention relates to an ophthalmic apparatus, and more particularly to an ophthalmic apparatus that irradiates the interior of a patient's eye with a beam of laser light, the apparatus being provided with an operating section that drives a deflection means whereby the beam of laser light is deflected by the operation of a lever.

2. Description of the Prior Art

An optical coagulator apparatus is an example of an ophthalmic apparatus of this type. Such an apparatus has an operating section with a lever. Movement of the lever causes a plane reflecting mirror to swing and thereby deflect a laser beam to illuminate a desired portion of a patient's eye.

However, the drawback of conventional optical coagulators is that the operating section is structurally complex and costly to manufacture, and there is also a need to improve the operability.

SUMMARY OF THE INVENTION

The object of the present invention is therefore to provide an ophthalmic apparatus that has an operating section which drives a means for deflecting a laser beam when an operating lever is manipulated, wherein the operating section is simple in construction, can be fabricated at a low cost and has good operability enabling the laser beam to be deflected with good precision.

In accordance with the present invention, an ophthalmic apparatus which irradiates the interior of a patient's eye with a beam of laser light and which includes an operating section for driving a deflection means that deflects the beam of laser light in accordance with the operation of an operating lever. The apparatus comprises a fixed ball member affixed to the operating section, a movable ball member integrally associated with one end of the operating lever and movably engaged with the fixed ball member in such a manner that the movable ball member is offset along the axial direction of the operating lever. The operating lever is supported over the fixed ball member in such a way that it can be tilted in a desired direction within a plane that is substantially orthogonal to the axis of the lever. The apparatus further comprises means for dividing movement of the movable ball member produced by tilting the operating lever into two orthogonal directions within said plane for transmission to the deflection means.

With the above arrangement, by tilting the operating lever in a desired direction the movable ball member is moved, and this movement divided into two orthogonal directions is transmitted to the deflection means to thereby deflect the laser beam. According to the apparatus of the invention, the operating section is structurally simple in construction, can be made at a low cost and has good operability enabling the laser beam to be precisely controlled.

Further features of the invention, its nature and various advantages will become more apparent from the accompanying drawings and following detailed description of the invention.

DETAILED DESCRIPTION OF THE INVENTION

Figure 1:
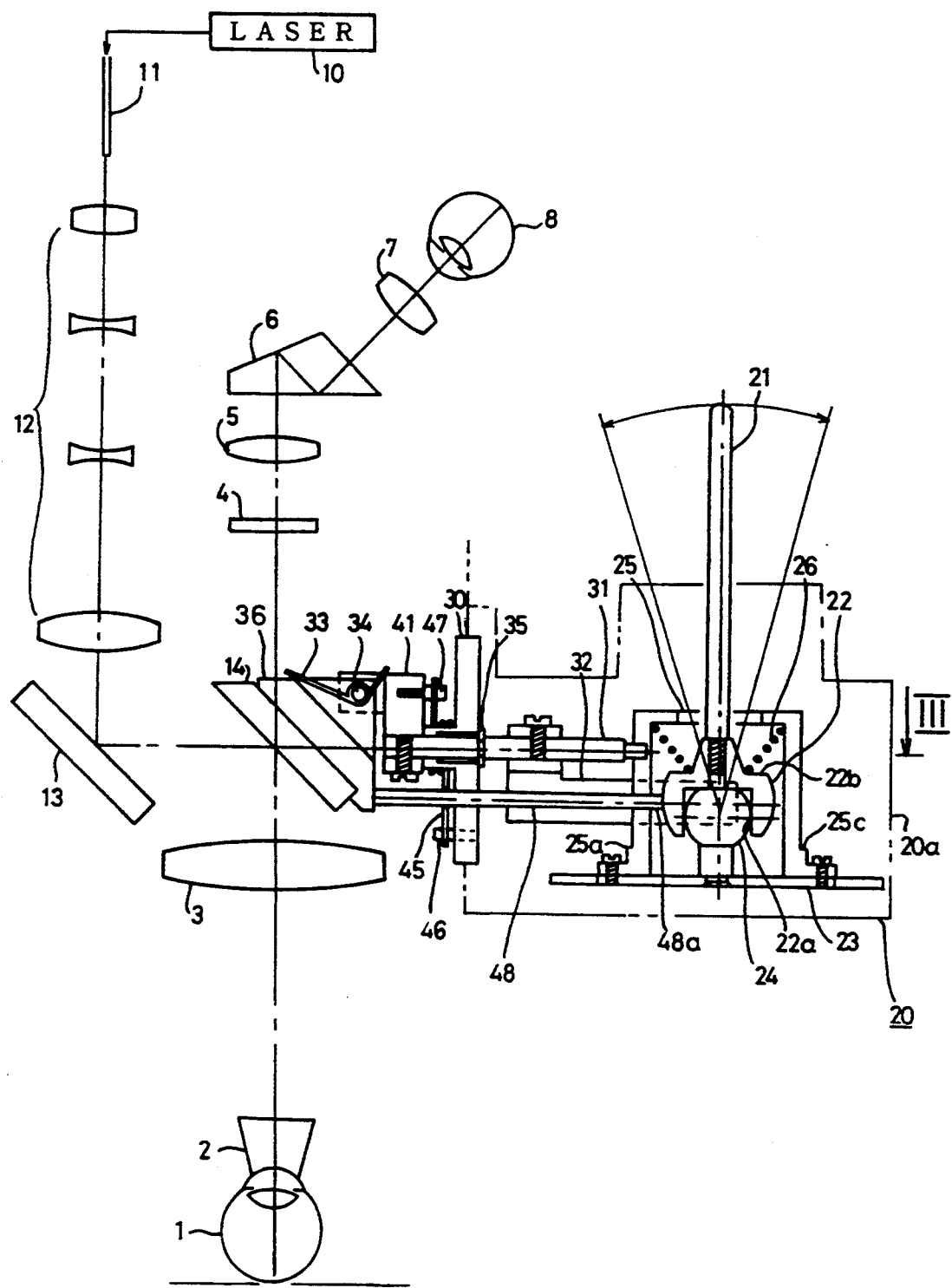
FIG. 1 shows the arrangement of the optical system and operating system of an optical coagulator apparatus according to an embodiment of the present invention.

FIG. 1 shows the arrangement of the optical system and operating section of an optical coagulator apparatus according to an embodiment of the present invention. In FIG. 1, a contact lens 2 is placed on an upward-looking eye 1 of a patient to neutralize the refractivity of the eye. Above the contact lens 2 is an objective lens 3 arranged so that it faces the contact lens 2. A beam of laser light (for focalization or treatment) emitted by a laser light source 10 passes along an optical fiber 11, is adjusted to a prescribed spot size by a telescopic lens system 12, deflected by deflecting means in the form of a fixed mirror 13 and a movable (swingable) mirror 14, and is formed into an image at a prescribed spot in the eye 1 by the objective lens 3.

Part of the laser light beam that is reflected from the cornea or image-forming surface of the eye 1 passes through the objective lens 3 and through both faces of the movable mirror 14, and is absorbed by a safety filter 4. However, when it is a focalizing beam the safety filter 4 can be retracted from the light path, whereby the focalizing beam passes through a microscope lens system consisting of an image formation lens 5, a prism 6 and an eyepiece 7 and enters the examiner's eye 8, providing the examiner with an enlarged view of the state of illumination by the laser beam.

During operation of the opthalmic apparatus, whereby the laser beam is deflected to produce an image at a specific spot in the patient's eye 1, an operating lever 21 of an operating section 20 is tilted in a desired direction, backwards or forwards or to either side. This causes the movable mirror 14 to swing in a direction, and by an amount, corresponding to this movement of the lever 21, thereby enabling the laser beam to be directed at the required spot of the patient's eye. Details of the operation of the operating section 20 will now be described.

Figure 3:
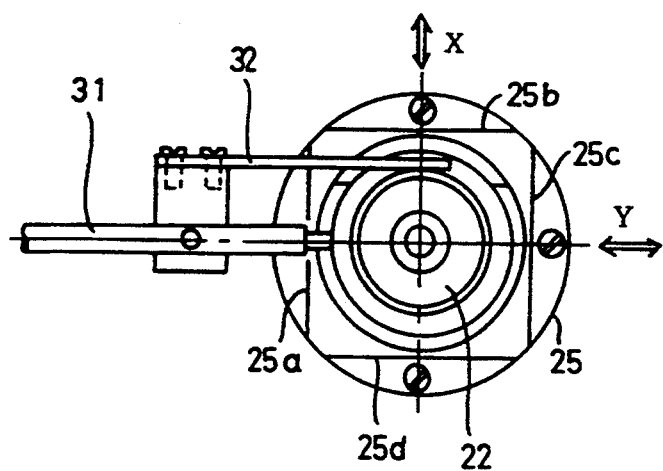
FIG. 3 is a plane cross-section through line a of the principle components of the operating lever unit of the embodiment of FIG. 1.

The operating lever 21 of the operating section 20 is supported so that it can be moved as desired within a plane that includes the X and Y directions indicated by the arrows in FIG. 3. That is, the lever 21 is supported in a way that allows it to be tilted in a desired direction in a plane substantially at right-angles to the axis of the operating lever 21.

Figure 2:
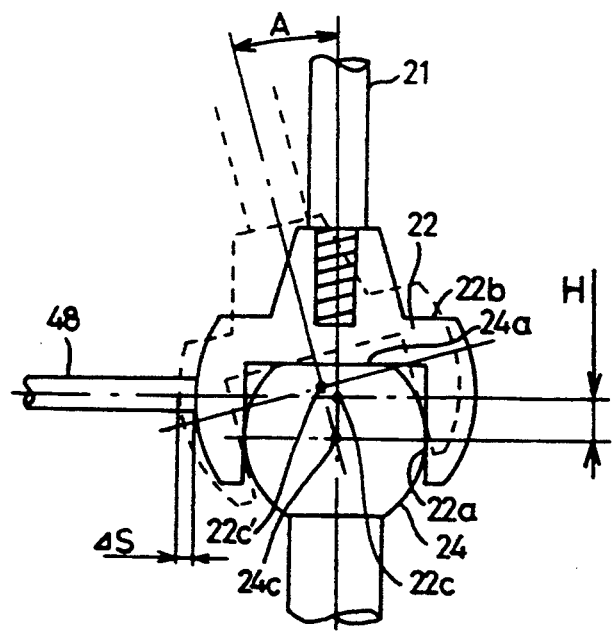
FIG. 2 is a view illustrating the operation of the movable ball member when the operating lever is manipulated.

Integrally affixed to the lower end of the operating lever 21 is a movable ball member 22 having a side portion that is substantially round. As shown in FIG. 2, formed in the movable ball member 22 is a recess 22a that opens downwards. The recess 22a is cylindrical in shape, with a flat upper surface, and a fixed ball member 24 locates movably into the recess 22a. That is, the movable ball member 22 fits movably onto the fixed ball member 24. The upper surface of the fixed ball member 24 is formed into a flat portion 24a, and the fixed ball member 24 is affixed onto a ball member base 23 that is attached to the body 20a of the operating section 20, as shown in FIG. 1.

As shown in FIG. 1, a tapered volute spring 26 is provided between the inner top-face of a ball member support frame 25 affixed to the ball member base 23, and a shoulder portion 22b formed on an upper part of the movable ball member 22. The force of the spring 26 urges the operating lever 21 to a vertical neutral position by pressing the flat upper surface of the recess 22a of the movable ball member 22 against the flat portion 24a of the fixed ball member 24. Thus, when only the force of the spring 26 is acting on the movable ball member 22, the force of the spring 26 holds the movable ball member 22 at a position at which the operating lever 21 is vertical in relation to the plane indicated by the X and Y directions shown in FIG. 3.

As shown by FIG. 2, the center 24c of the fixed ball member 24 and the center 22c of the movable ball member 22 are offset along the axial line of the operating lever 21 by an amount H. The effect of this offset is that when the operating lever 21 is tilted, for example by the angle indicated by A in FIG. 2, the center 22c of the movable ball member 22 is moved to the position indicated by 22c', moving the movable ball member 22 to the left (with reference to the drawing) by a fine distance ΔS. A link plate 32 and link shaft 48 are provided to transfer this fine motion into two orthogonal directions, X and Y axes for transmission to the movable mirror 14.

Referring to FIGS. 1 and 2, the link plate 32 is affixed to a turning shaft 31. The turning shaft 31 is rotatably supported by the ball member support frame 25 and a bearing 30 that is attached to the body 20a. The end of the turning shaft 31 on the left side (with reference to FIG. 1) is anchored to a mirror support member 41 and has a snap-ring 35 on the other side of the bearing 30, thereby preventing the turning shaft 31 from moving in the axial direction.

The movable mirror 14 is held by a mirror holder 36 that is swingably mounted on a shaft 34 attached to the mirror support member 41. A spring 33 on the shaft 34 urges the mirror holder 36 counterclockwise (with reference to FIG. 1), pressing the lower end of the mirror holder 36 into contact with the left end (in FIG. 1) of the link shaft 48. The link shaft 48 can move horizontally, with reference to the drawing, and is therefore moved to the right, causing the right end of the shaft 48 to press against the peripheral surface of the movable ball member 22. Thus, the fine movement of the movable ball member 22 in the Y direction (FIG. 3) is transmitted, without any play, to the movable mirror 14, whereby the movable mirror 14 is pivoted clockwise or counterclockwise on the shaft 34 by an amount that corresponds to the amount by which the movable ball member 22 is moved in the Y direction by the operation of the operating lever 21.

A spring 45 is disposed between a pin 46 set into the bearing 30 and another pin 47 set into the mirror support member 41. This spring 45 urges the turning shaft 31 counterclockwise towards the movable ball member 22, whereby the link plate 32 attached to the turning shaft 31 is pressed against the outer peripheral surface of the movable ball member 22. Thus, the fine movement of the movable ball member 22 in the X direction is transmitted as the rotation of the turning shaft 31 to the movable mirror 14 without any play, whereby the movable mirror 14 is turned about the turning shaft 31 by an amount that corresponds to the amount by which the movable ball member 22 is moved in the X direction by the operation of the operating lever 21.

In accordance with this arrangement, by manipulating the operating lever 21 in a plane that includes the X and Y directions (FIG. 3), that is, by tilting the operating lever 21 in a desired direction in a plane at right-angles to the lever 21, the examiner can pivot the movable mirror 14 clockwise or counterclockwise about the shaft 34, or turn the mirror about the turning shaft 31, thereby deflecting the laser beam reflecting from the movable mirror 14 as desired, enabling the examiner to use the laser beam spot image to illuminate a desired portion of the patient's eye 1 within a microscopic field of view.

When the examiner releases the operating lever 21 the force of the volute spring 26 brings the operating lever 21 to its vertical position by urging the flat upper surface of the recess 22a of the movable ball member 22 against the flat portion 24a of the fixed ball member 24, whereby the laser beam spot image also comes to a rest in the center part of the field of view.

The operating section 20 is provided with a control arrangement for focusing the laser beam light spot on the focal point of the microscope, and for controlling an X-Y movement device (not shown) for moving the field of view in the X and Y directions. This arrangement will now be described with reference to FIGS. 4, 5 and 6.

Figure 4:
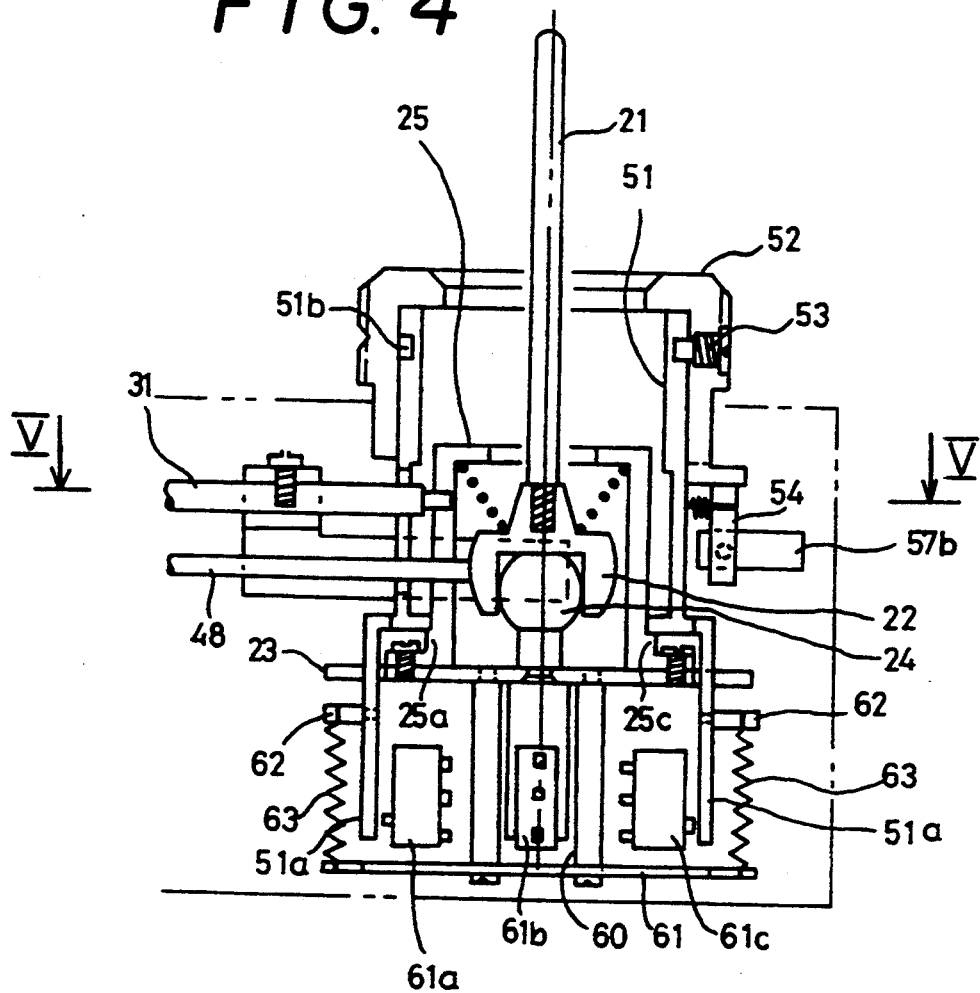
FIG. 4 is an overall cross-sectional side view of the operating lever unit.
Figure 5:
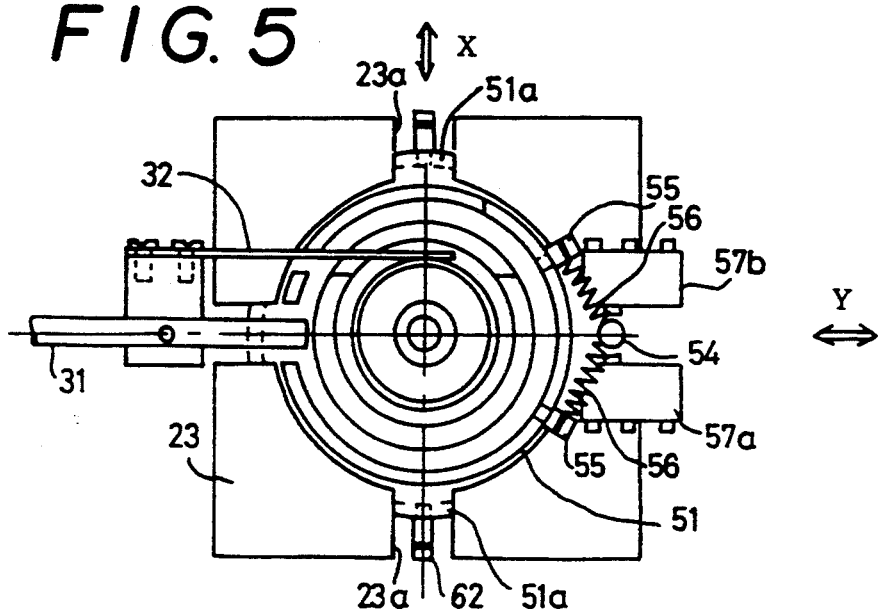
FIG. 5 is a plane cross-section through line b of the operating lever unit of FIG. 4.
Figure 6:
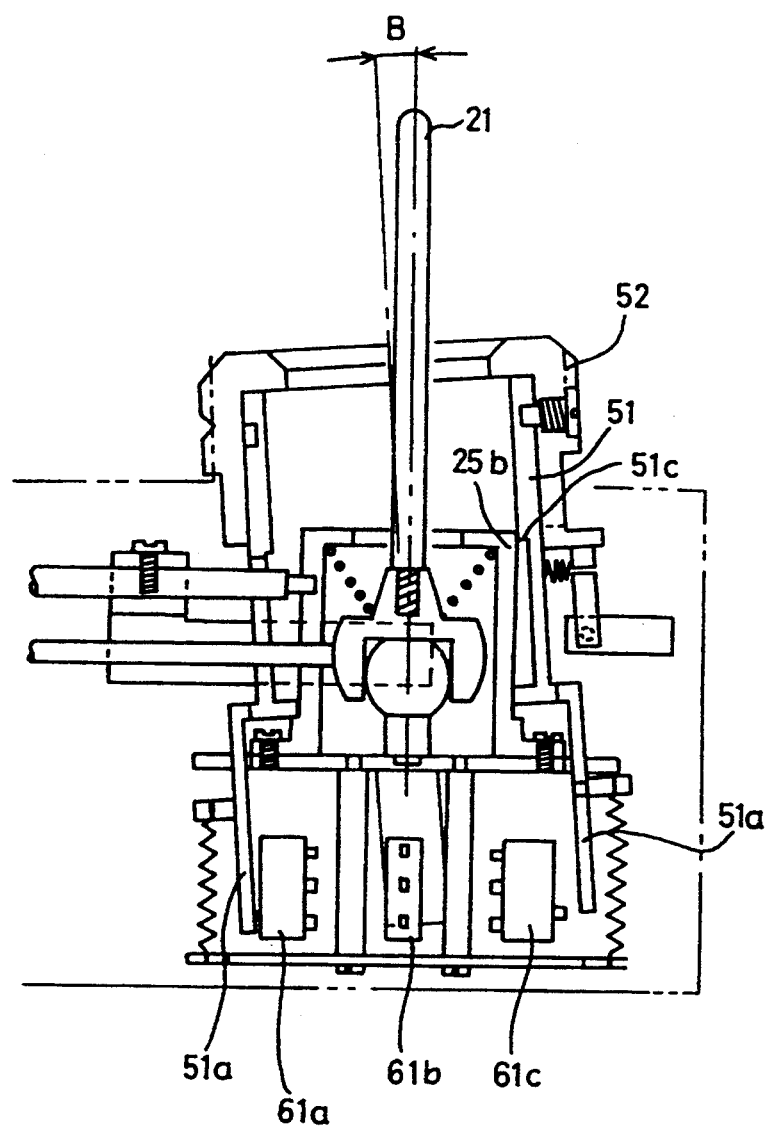
FIG. 6 is a cross-sectional side view illustrating the tilting operation of the operating ring of the operating lever unit.

In FIGS. 4 to 6, reference numeral 51 denotes an operating member in the form of a generally cylindrical tilt shaft with a diameter larger than that of the operating lever 21. The tilt shaft 51 is arranged substantially concentrically with the operating lever 21 and fits over the ball member support frame 25 that is affixed on the ball member base 23, as shown in FIG. 4. The tilt shaft 51 is held in contact with stepped portions 25a to 25d (FIG. 3) of the ball member support frame 25 by the force of four springs 63 provided between a spring holder 61 affixed to posts 60 attached to the lower surface of the ball member base 23, and four pins 62 set into leg portions 51a that extend downward from the tilt shaft 51.

In accordance with this arrangement, the tilt shaft 51 can be tilted backwards and forwards (the Y direction in FIG. 5) and to the left and right (the X direction in FIG. 5). When not subjected to an external force the tilt shaft 51 is brought to rest to a neutral position, in relation to the plane indicated by the X and Y directions shown in FIG. 5 by the force of the springs 63 urging the lower peripheral edge of the tilt shaft 51 into contact with the stepped portions 25a to 25d. To facilitate tilting the shaft 51 in any of the four directions the stepped portions 25a to 25d have been formed into a square, as shown by FIG. 3.

As shown in FIG. 5, the four leg portions 51a fit loosely into four corresponding grooves 23a formed in the ball member base 23, which prevents the tilt shaft 51 from rotating. An operating ring 52 is movably located on the outer surface of the tilt shaft 51. The operating ring 52 is retained in place by a shaft 53 that is disposed on the inner side of the ring 52 and engages with a groove 51b formed in the tilt shaft 51.

The operating ring 52 has a pin 54 which extends downward. As shown by FIG. 5, there are two springs 56 which extend from the pin 54 to a pair of pins 55 provided on the outer surface of the tilt shaft 51. The rotatable operating ring 52 is held at a point where the tension of the two springs 56 is in balance. Two microswitches 57a and 57b are each arranged at a position whereby rotation of the pin 54 will bring the pin 54 into contact with one of the microswitches.

The microswitches 57a and 57b are used to perform control functions such as the focusing operation described above. For example, when the examiner rotates the operating ring 52 clockwise (in the case of FIG. 5), microswitch 57a is switched on by the pin 54, bringing the microscope closer to the beam spot, while when the operating ring is rotated counterclockwise the microswitch 57b is switched on, causing the microscope to move away from the beam spot. When the examiner releases the ring 52, and the pin 54 return to the rest position at which both microswitches are off, halting the focusing control operation.

In addition to being rotatable, the operating ring 52 can be moved with the tilt shaft 51 in the X and Y directions to control, for example, an X-Y movement device. This control is exercised by means of four microswitches provided below the ball member base 23. Three of these microswitches are denoted by reference numerals 61a to 61c; the fourth microswitch is not shown.

With reference to FIG. 6, when the examiner tilts the operating ring 52 forwards by a prescribed angle B the leg portion 51a on the left side (in the drawing) switches on the microswitch 61a and the microscope field of view is moved forward by the X-Y movement device (not shown). The microscope can be thus moved in the direction in which the operating ring 52 is tilted. The tilt angle B is limited by the mid-section 51c of the tilt shaft 51 coming into contact with the shoulder portion 25b of the ball member support frame 25. When the examiner releases the operating ring 52, the ring 52, together with the tilt shaft 51, is returned to the neutral vertical position by the tension of the springs 63, halting the movement of the microscope.

With the apparatus according to this embodiment, the operating section 20 is structurally simple in construction and can be produced at a low cost. Also, the examiner can check in the field of view of the microscope while manipulating the operating lever 21 to precisely deflect the laser beam to illuminate the desired spot in the patient's eye. Also, the focusing operation and positioning of the microscope can be effected by turning and tilting the operating ring 52 arranged concentrically with the operating lever 21, so that the basic operations of optical coagulation treatment can be performed using just one hand and without requiring the release of the operating section 20. In addition, the operating ring 52 can be used to guide the hand when making fine movements of the operating lever 21. Thus, the apparatus according to this invention provides excellent operability.

While in the above arrangement a movable mirror is the means used to deflect the laser beam, it is to be understood that a prism or other such means may be used instead. Also, the invention is not limited to an optical coagulator apparatus. Instead, the above operating lever unit arrangement may be applied to other ophthalmic apparatuses that are provided with an operating unit that drives a means for deflecting a laser beam into a patient's eye in accordance with the manipulation of an operating lever.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmic apparatus for irradiating the interior of a patient's eye with a laser beam, said apparatus comprising: means for deflecting a laser beam to the interior of a patient's eye; and an operating section for driving said deflecting means to deflect a laser beam at a selected spot in a patient's eye, said operating section comprising a base member, a fixed ball member affixed to said base member, a movable ball member having a recess for receiving said fixed ball member, an operating lever fixed at a first end thereof to said movable ball member such that said operating level can be tilted in a desired direction within a plane that is substantially orthogonal to the axis of said operating lever, said movable ball member being movably engaged with said fixed ball member such that the movable ball member is offset along the axial direction of the operating lever, and means for transferring movements of the movable ball member produced by tilting the operating lever into first and second orthogonal directions within said plane to said deflecting means.

2. An ophthalmic apparatus as set forth in claim 1; wherein said fixed ball member and said movable ball member are disposed within a support frame affixed to said base.

3. An ophthalmic apparatus as set forth in claim 2; wherein said recess in said movable ball member is formed with a flat upper surface and the upper surface of the fixed ball member is formed as a flat portion, and further comprising a resilient member disposed within said support frame for urging said upper surface of said recess into contact with said flat portion.

4. An ophthalmic apparatus as set forth in claim 2; wherein said means for transferring comprises a turning shaft including a first end rotatably supported by said support frame and a second end supporting an upper portion of said deflecting means, a link plate having a first end affixed to said turning shaft between said first and second ends of said turning shaft and a second end in contact with said movable ball member a link shaft having a first end in contact with said movable ball member and a second end in contact with a lower portion of said deflecting means, wherein movement of said operating lever in said first and second orthogonal directions is transmitted by said turning shaft and said link shaft, respectively, to said deflecting means for deflecting a laser beam.

5. An ophthalmic apparatus as set forth in claim 1; further comprising a generally cylindrical operating member having a diameter larger than said operating lever and being arranged substantially concentrically with said operating lever, wherein movement of said operating lever in said first and second orthogonal directions permits an examiner to view the interior of a patient's eye as the patient's eye is irradiated with a laser beam.

6. An ophthalmic apparatus for irradiating the interior of a patient's eye with a laser beam within a microscopic field of view, said apparatus comprising: a laser source for producing a laser beam; a laser beam projector for projecting the laser beam; means for deflecting the laser beam to the interior of a patient's eye; means for driving said deflecting means to deflect the laser beam at a selected spot in a patient's eye; and means coupled to said driving means for focusing the laser beam at a focal point of a microscope and for positioning the microscope within the field of view of said selected spot in a patient's eye, wherein said driving means comprises a base member, a fixed ball member affixed to said base member, a movable ball member having a recess for receiving said fixed ball member, an operating lever integrally fixed at a first end thereof to said movable ball member such that said operating lever can be tilted in a desired direction within a plane that is substantially orthogonal to the axis of said operating lever, said movable ball member being movably engaged with said fixed ball member such that the movable ball member is offset along the axial direction of the operating lever, and means for transferring movements of the movable ball member produced by tilting the operating lever into first and second orthogonal directions within said plane to said deflecting means.

7. An ophthalmic apparatus as set forth in claim 6; wherein said recess in said movable ball member is formed with a flat upper surface and the upper surface of the fixed ball member is formed as a flat portion, and further comprising a resilient member disposed within said support frame for urging said upper surface of said recess into contact with said flat portion.

8. An ophthalmic apparatus as set forth in claim 7; wherein said means for focusing and positioning means comprises a generally cylindrical operating member having a diameter larger than said operating lever and being arranged substantially concentrically with said operating lever, wherein movement of said operating lever in said first and second orthogonal directions permits an examiner to view the interior of a patient's eye as the patient's eye is irradiated with said laser beam.

9. An operating section for driving a deflection means in an ophthalmic apparatus for irradiating the interior of a patient's eye with a laser beam, said operating section comprising: a base member, a fixed ball member affixed to said base member, a movable ball member having a recess for receiving said fixed ball member, an operating lever fixed at a first end thereof to said movable ball member such that said operating level can be tilted in a desired direction within a plane that is substantially orthogonal to the axis of said operating lever, said movable ball member being movably engaged with said fixed ball member such that the movable ball member is offset along the axial direction of the operating lever, and means for transferring movements of the movable ball member produced by tilting the operating lever into first and second orthogonal directions within said plane to said deflecting means.

10. An operating section as set forth in claim 9; wherein said fixed ball member and said movable ball member are disposed within a support frame affixed to said base.

11. An operating section as set forth in claim 10; wherein said recess in said movable ball member is formed with a flat upper surface and the upper surface of the fixed ball member is formed as a flat portion, and further comprising a resilient member disposed within said support frame for urging said upper surface of said recess into contact with said flat portion.

12. An operating section as set forth in claim 10; wherein said means for transferring comprises a turning shaft including a first end rotatably supported by said support frame and a second end supporting an upper portion of said deflecting means, a link plate having a first end affixed to said turning shaft between said first and second ends of said turning shaft and a second end in contact with said movable ball member, a link shaft having a first end in contact with said movable ball member and a second end in contact with a lower portion of said deflecting means, wherein movement of said operating lever in said first and second orthogonal directions is transmitted by said turning shaft and said link shaft, respectively, to said deflecting means for deflecting a laser beam.

13. An operating section as set forth in claim 9; further comprising a generally cylindrical operating member having a diameter larger than said operating lever and being arranged substantially concentrically with said operating lever, wherein movement of said operating lever in said first and second orthogonal directions permits an examiner to view the interior of a patient's eye as the patient's eye is irradiated with a laser beam.

* * * * *